(12) United States Patent
Sorns et al.

(10) Patent No.: US 7,879,915 B2
(45) Date of Patent: Feb. 1, 2011

(54) EMULSIONS FOR FINISHING TEXTILES AND PAPER

(75) Inventors: Jorg Sorns, Duesseldorf (DE); Rolf Kawa, Monheim (DE); Stephen Eichhorn, Gernsheim (DE); Andrea Urban, Ludwigshafen (DE)

(73) Assignee: Cognis IP Management GmbH, Duesseldorf (DE)

( * ) Notice: Subject to any disclaimer, the term of this patent is extended or adjusted under 35 U.S.C. 154(b) by 46 days.

(21) Appl. No.: 12/518,194

(22) PCT Filed: Nov. 29, 2007

(86) PCT No.: PCT/EP2007/010349

§ 371 (c)(1),
(2), (4) Date: Jun. 8, 2009

(87) PCT Pub. No.: WO2008/067944

PCT Pub. Date: Jun. 12, 2008

(65) Prior Publication Data

US 2010/0242796 A1 Sep. 30, 2010

(30) Foreign Application Priority Data

Dec. 8, 2006 (EP) .................... 06025405

(51) Int. Cl.
*D21H 21/24* (2006.01)
*D21H 27/00* (2006.01)
*D21H 17/20* (2006.01)
*A61K 8/00* (2006.01)
*D06M 15/00* (2006.01)

(52) U.S. Cl. .............. 516/29; 106/250; 106/287.26; 162/179; 252/8.61; 252/8.62; 252/8.63; 252/8.81; 252/8.91; 516/21; 516/28

(58) Field of Classification Search ........... 106/250, 106/287.26; 252/8.61, 8.62, 8.63, 8.81, 8.91; 516/21, 28, 29; 162/179
See application file for complete search history.

(56) References Cited

U.S. PATENT DOCUMENTS

| 3,896,807 | A | | 7/1975 | Buchalter | |
|---|---|---|---|---|---|
| 4,112,167 | A | | 9/1978 | Dake et al. | |
| 4,786,367 | A | | 11/1988 | Bogart et al. | |
| 5,399,271 | A | | 3/1995 | Puchta et al. | |
| 6,419,938 | B1 | * | 7/2002 | Riedel et al. | 424/401 |
| 6,511,655 | B1 | * | 1/2003 | Muller et al. | 424/59 |
| 6,558,680 | B1 | * | 5/2003 | Riedel et al. | 424/401 |
| 2004/0029977 | A1 | * | 2/2004 | Kawa et al. | 514/786 |

FOREIGN PATENT DOCUMENTS

| DE | 10102500 A1 | | 8/2002 |
|---|---|---|---|
| DE | 10245727 A1 | * | 4/2004 |
| EP | 1225276 A1 | | 7/2002 |
| EP | 1557153 A1 | * | 7/2005 |
| GB | 2069333 A | | 8/1981 |
| WO | 9516824 A1 | | 6/1995 |
| WO | 9535411 A1 | | 12/1995 |
| WO | 9535412 A1 | | 12/1995 |
| WO | 9730216 A1 | | 8/1997 |
| WO | WO03/068182 A1 | * | 8/2003 |

OTHER PUBLICATIONS

V. Zeidler, "Über das Spreiten von Lipiden auf der Haut" Fette-Seifen-Anstrichmittel No. 10, 1985, pp. 403-408.

* cited by examiner

*Primary Examiner*—Anthony J Green
(74) *Attorney, Agent, or Firm*—Fox Rothschild LLP

(57) ABSTRACT

The invention provides water-in-oil emulsions containing (a) 12-21% by weight of polyglyceryl-2 dipolyhydroxystearate, (b) 4-7% by weight of a hydrogenated ethoxylated castor oil, (c) 25-35% by weight of mineral oil, (d) 20-30% by weight of further oil substances (e), 3-5% by weight of hydrotropes, (f) 3-4% by weight of metal soaps and (g) 10-30% by weight of water, based on the overall composition. The emulsions are useful for finishing textiles and papers.

11 Claims, No Drawings

EMULSIONS FOR FINISHING TEXTILES AND PAPER

CROSS REFERENCE TO RELATED APPLICATIONS

This application is the National Stage entry of PCT/EP2007/010349, filed Nov. 29, 2007, which claims priority to European patent application number EP 06025405, filed Dec. 8, 2006, both of which are incorporated herein by reference in their entireties.

FIELD OF THE INVENTION

The invention relates to specific emulsions which can be used for impregnating and wetting commodity and hygiene paper towels.

BACKGROUND OF THE INVENTION

The general term "paper" is understood as meaning about 3000 different types and articles whose nature and fields of use in some cases differ considerably. For the production of paper, a number of additives are required, of which fillers (i.e. chalk or kaolin) and binders (e.g. starch) are among the most important. For the area of tissue and hygiene papers which are brought into relatively close contact with human skin, there is a particular need for a pleasant soft feel which is usually imparted to the paper by a careful choice of the fibers and in particular a high proportion of fresh groundwood or cellulose. With regard to the cost-efficiency of papermaking and from an ecological point of view, however, it is desirable also to use as high proportions as possible of low-quality waste paper. However, the result of this is that the soft feel of the paper is adversely affected to a significant extent, which is found to be troublesome by the users and, in particular with frequent use, can also lead to skin irritations.

In the past, there has therefore been no lack of attempts to modify tissue papers by impregnation, coating or other surface treatment so that a pleasant soft feel results. Special lotions and emulsions which firstly can be easily be applied to the paper and secondly do not adversely affect the paper structure must be developed for this purpose. In order to improve the soft feel, frequently nonionic surfactants or a combination of nonionic and anionic surfactants are used. Polysiloxanes and cationic polymers are also used for this purpose.

International patent application WO 95/35411 relates to tissue papers which are coated with finishing compositions which contain from 20 to 80% by weight of an anhydrous emollient (mineral oils, fatty acid esters, fatty alcohol ethoxylates, fatty acid ethoxylates, fatty alcohols and mixtures thereof), from 5 to 95% by weight of an emollient-immobilizing agent (fatty alcohols, fatty acids or fatty alcohol ethoxylates having in each case 12 to 22 carbon atoms in the fat radical) and from 1 to 50% by weight of surfactants having an HLB value of, preferably, from 4 to 20. The working examples mentioned in the document contain without exception petrolatum as the emollient. International patent application WO 95/35412 discloses similar tissue papers, anhydrous mixtures of (a) mineral oils, (b) fatty alcohols or fatty acids and (c) fatty alcohol ethoxylates being used as softeners. International patent application WO 95/16824 relates to finishing compositions for tissue papers which contain mineral oil, fatty alcohol ethoxylates and nonionic surfactants (sorbitan esters, glucamides). Furthermore, international patent application WO 97/30216 (Kaysersberg) describes liquid finishing compositions for paper tissues based on long-chain, saturated fatty alcohols and wax esters having altogether at least 24 carbon atoms, which finishing compositions contain a very high proportion of water. From the point of view of use, soft feel, processing behavior and sensory properties of the treated papers are still worthy of improvement. DE 10102500 A1 relates to lotions which contain (a) polyol poly-12-hydroxystearates, (b) oily substances selected from the group consisting of the glycerides, hydrocarbons, silicone oils, dialkyl ethers and dialkyl carbonates, or any desired mixtures thereof, and (c) 5-25% by weight of water and are suitable, as described in EP 1 225 276 A1, also for the coating of papers. These emulsions and lotions are still worthy of improvement with respect to the stability. In particular, it is frequently not possible to incorporate plant extracts without a color change, which has a disadvantageous effect on the whiteness of the paper to be coated.

It was the object of the invention to provide emulsions having improved stability and with the aid of which dry commodity papers, in particular tissue papers, but also reinforced tissue can be coated without significantly reducing the whiteness of the paper. The emulsions should have excellent care properties, and should resemble classical skin care formulations with regard to sensory properties. A further aspect of the object is to provide preparations which are also compatible with tissue papers with a high proportion of waste paper. At the same time, only readily biodegradable auxiliaries should be used and the preparations should penetrate easily into the tissue, be homogeneously distributed, have a relatively low water content and, in highly concentrated form, nevertheless have such a low viscosity that they can be readily processed.

DETAILED DESCRIPTION OF PREFERRED EMBODIMENTS

It has now surprisingly been found that preparations based on certain emulsifiers, a high proportion of mineral oils and a defined water content not only ensure a pleasant soft feel of the paper products but are also more stable than the known coating lotions/emulsions of the prior art. Even on incorporation of plant extracts which have an intrinsic color, the whiteness of the paper does not significantly decrease on coating of the paper with the lotions according to the invention.

The invention therefore relates to W/O emulsions containing:
- (a) 12-21% by weight of polyglyceryl 2-dipolyhydroxystearate
- (b) 4-7% by weight of a hydrogenated ethoxylated castor oil
- (c) 25-35% by weight of mineral oil
- (d) 20-30% by weight of further oily substances
- (e) 3-5% by weight of hydrotropes
- (f) 3-4% by weight of metal soaps and
- (g) 10-30% by weight of water based on the total composition.

The emulsions according to the invention are liquid, pumpable at 20° C. and therefore very easily processible. Owing to the high proportion of oils, the emulsions have good care properties and are substantially more stable than comparable emulsions of the prior art which are used for coating. They are distinguished by less influence of the whiteness of the paper material to be coated and produce a good sensory smoothness on the skin. The components of the emulsion must be exactly tailored to one another; preferably, the emulsions according to the invention contain no further constituents apart from byproducts relating to the raw materials, i.e. the emulsions substantially comprise the components (a) to (g) in the stated amounts. It has been found that only mixtures in the stated ratios meet the stability requirements, are capable of taking up active substances having an intrinsic color, such as, for example, herbal chamomile, without leading to a significant change in the whiteness of the coated paper. For example, Dehymuls® PGPH from Cognis Deutschland GmbH and Co. KG can be used as component (a). Emulsions which are characterized in that, on coating of papers and nonwovens, the decrease in the whiteness of the paper/nonwoven is not more than 4%, in particular not more than 3.5%, are particularly preferred according to the invention. The whiteness is measured by the method DIN EN 12625-7, point 7.3.2, color (D 65/10°), the whiteness of uncoated/unimpregnated paper corresponding to 100%.

In a preferred embodiment, the emulsions have a viscosity of 500-5000 mPa·s at 23° C., a range of 500-3000 mPa·s and in particular 1000-2000 mPa·s being preferred (Brookfield RVF, spindle 5, 10 rpm, 23° C.)

The emulsions contain a proportion of water of not more than 30% by weight, based on the total composition. A water content of not more than 25% by weight and particularly preferably not more than 20% by weight is preferred according to the invention. The total amount of the emulsifiers (a) and (b) may vary from 16 to 28% by weight, based on the total composition, and is preferably 15-25% by weight. According to the invention, it is preferable if the weight ratio of the components (a:b) varies in the range (2.5-3.5):1. An ethylene oxide adduct of 7 mol of ethylene oxide per mole of hydrogenated castor oil is preferred as component (b). Such a product is, for example, Dehymuls® HRE 7, which is marketed by Cognis Deutschland GmbH & Co. KG.

Oily Substances: Components (c) and (d)

The total amount of the oily substances (c) and (d) varies from 45 to 65% by weight. In a preferred embodiment, the proportion of the mineral oil, based on the oil phase, is at least 45% by weight, preferably at least 50% by weight and in particular at least 55% by weight, based on the total amount of the components (c) and (d). The oil phase should have as low a viscosity as possible, i.e. oily substances having viscosities of 2-230 mPa·s are preferred, in particular as oily substances (d). The following mineral oils are suitable as component (c): white oil Pharma 40, low-viscosity paraffin oil, high-viscosity paraffin oil, liquid paraffin, paraffinum perliquidum, paraffinum subliquidum.

For example, the classes of compounds stated below are suitable as further oily substances (component d): Guerbet alcohols based on fatty alcohols having 6 to 18, preferably 8 to 10, carbon atoms, e.g. 2-ethylhexanol or 2-octyldodecanol; esters of linear or branched, saturated or unsaturated $C_6$-$C_{24}$-fatty acids with linear or branched, saturated or unsaturated $C_6$-$C_{24}$-fatty alcohols. Hexyl laurate, myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate, erucyl isostearate, erucyl oleate, cococaprylate/caprate may be mentioned by way of example. Further suitable esters are, for example, esters of $C_{18}$-$C_{38}$-alkylhydroxycarboxylic acids with linear or branched, saturated or unsaturated $C_6$-$C_{22}$-fatty alcohols, esters of linear or branched, saturated or unsaturated fatty acids with polyhydric alcohols (such as, for example, propylene glycol, dimer diol or trimer triol) and/or Guerbet alcohols, triglycerides or triglyceride mixtures, liquid mono-/di-/triglyceride mixtures, esters of $C_6$-$C_{22}$-fatty alcohols and/or Guerbet alcohols with aromatic carboxylic acids, in particular benzoic acid (e.g. Finsolv® TN), esters of $C_2$-$C_{12}$-dicarboxylic acids with linear or branched, saturated or unsaturated alcohols having 1 to 22 carbon atoms or polyols having 2 to 10 carbon atoms and 2 to 6 hydroxyl groups. Vegetable oils, triglyceride mixtures, substituted cyclohexanes, linear symmetrical or asymmetrical dialkyl carbonates (e.g. Cetiol® CC), Guerbet carbonates based on fatty alcohols having 6 to 18, preferably 8 to 10, C atoms, linear or branched, symmetrical or asymmetrical dialkyl ethers having 6 to 22 carbon atoms per alkyl group, such as, for example, di-n-octyl ether (Cetiol® OE), ring-opening products of epoxidized fatty acid esters with polyols, hydrocarbons, such as paraffin or mineral oils, oligo- or poly-alpha-olefins, are also suitable. The dialkyl carbonates and dialkyl ethers may be symmetrical or asymmetrical, branched or straight-chain, saturated or unsaturated and can be prepared by reactions which are sufficiently well known from the prior art. Suitable silicone compounds are, for example, dimethylpolysiloxanes, methylphenylpolysiloxanes, cyclic silicones (cyclomethicone) and amino-, fatty acid-, alcohol-, polyether-, epoxy-, fluorine-, glycoside- and/or alkyl-modified silicone compounds. Simethicones are furthermore suitable.

In particular, oils having spreading values of at least 250 mm$^2$/10 min (U. Zeidler: Über das Spreiten von Lipiden auf der haut, Fette-Seifen-Anstrichmittel [On the spreading of lipids on the skin, fats-soaps-coating materials] No. 10, 403-408, 1985), in particular ester oils, dialkyl ethers, Guerbet alcohol or glycerides having the abovementioned spreading value, are preferred as component (d). These include, for example, dibutyl adipate, isopropyl palmitate, hexyl laurate, ethylhexyl stearate, dicaprylyl ether, dicaprylyl carbonates, hexyldecyl stearate, oleyl oleate, oleyl erucate or vegetable oils.

Hydrotropes (e)

The emulsions according to the invention contain, as component (e), at least one hydrotrope which contributes to the improvement of the sensory properties and stability of the composition and has solubilizing properties. It also serves for keeping the moisture content of the emulsion stable in the paper.

According to the invention, liquid polyols and polyol derivatives, e.g. glycerol, diglycerol, triglycerol, ethylene glycol, propylene glycol, butylene glycol, 1,2,6-hexanetriol and liquid polyethylene glycols, are suitable. Glycerol, diglycerol and triglycerol are preferred according to the invention. The hydrotrope is present in amounts of 3-5% by weight, in particular 3.5-4.5% by weight, based on the total composition. Glycerol, butylene glycol or propylene glycol, and among these glycerol, are preferred according to the invention.

Metal Soaps (f)

The term "metal soaps" is understood by the person skilled in the art as meaning not very water-soluble metal salts of fatty acids (cf. Römpps Chemielexikon [Römpps Chemistry Lexikon]). Owing to their oil-thickening properties, they make a synergistic contribution to the stability of the emulsion. Calcium, magnesium, aluminum and zinc salts of C12-C24-fatty acids or $C_{12}$-$C_{24}$-hydroxy fatty acids are usually suitable. According to the invention, preferred metal soaps are magnesium stearate and/or aluminum stearate. Owing to their structural formation, the latter are particularly suitable for thickening and stabilizing the oil phase.

Irritation-Relieving/Antiinflammatory Active Substances

A preferred embodiment of the emulsion according to the invention contains at least one irritation-relieving/antiinflammatory active substance which serves in particular for relieving inflammatory skin processes or reddened, chafed skin. The irritation-relieving active substance is usually present in an amount of 0.01-10% by weight, preferably 0.05-5% by weight, and in particular 0.05-3% by weight.

In particular, bisabolol, allantoin and panthenol are preferred according to the invention. Vitamins and vitamin precursors and protein hydrolysis products can also promote the healing of wounds.

Plant extracts, which frequently contain a synergistic combination of wound-healing/irritation-relieving substances, are also suitable. These extracts are usually prepared by extraction of the entire plant. In individual cases, however, it may also be preferable to prepare the extracts exclusively from flowers and/or leaves of the plant.

According to the invention, in particular the extracts of camomile, aloe vera, witch hazel, lime-tree blossoms, sage and melissa are suitable.

EXAMPLE

Two formulations, a formulation (1) according to the invention and a comparative formulation (C1), were rated with regard to stability and whiteness. The whiteness was measured by method DIN EN 12625-7, point 7.3.2, color) (D65/10°), the whiteness of uncoated/unimpregnated paper being rated at 100%. The decrease in whiteness in % was rated, the decrease not being permitted to be more than 4%. The sensory properties were rated by trained persons on the basis of the principle of school marks from 1 to 6.

| Ingredients | 1 | C1 |
|---|---|---|
| Polyglyceryl 2-dipolyhydroxystearate | 15 | 20.6 |
| Hydrogenated castor oil + 7EO | 5 | — |
| Mineral oil | 30 | — |
| Ethylhexyl stearate | 22.4 | — |
| Cocoglyceride | — | 20.6 |
| Dicaprylyl ether | — | 20.6 |
| Sorbitan sesquioleate | — | 4.8 |
| Beeswax | — | 3.35 |
| Dicocoyl pentaerythrityl distearyl citrate | — | 2 |
| Tocopherol and hydrogenated palm glyceride citrate | — | 0.02 |
| Glycerol | 4 | 7 |
| Magnesium stearate | 3.5 | — |
| Aluminum stearate | — | 2.75 |
| *Chamomilla recutita* (*matricaria*) flower extract | 0.1 | 0.1 |
| Water | 20 | 18.2 |
| Preservative | as desired | |
| Appearance | milky white | milky yellow |
| Stability 4 weeks - RT | + | + |
| Stability 8 weeks - RT | + | — |
| Stability 4 weeks - 30° C. | + | — |
| Decrease in whiteness in % | 3.4 | 3.9 |
| Sensory properties of the lotion - creaminess | 1.0 | 4.0 |

What is claimed is:

1. A water-in-oil emulsion comprising:
   (a) 12-21% by weight of polyglyceryl 2-dipolyhydroxystearate;
   (b) 4-7% by weight of a hydrogenated ethoxylated castor oil;
   (c) 25-35% by weight of mineral oil;
   (d) 20-30% by weight of one or more additional oily substances;
   (e) 3-5% by weight of one or more hydrotropes;
   (f) 3-4% by weight of one or more metal soaps; and
   (g) 10-30% by weight of water,
   wherein all weight % are based on the emulsion.

2. The emulsion of claim 1, wherein component (b) comprises an ethylene oxide adduct of 7 mol of ethylene oxide per mole of hydrogenated castor oil.

3. The emulsion claim 1, wherein the total amount of the emulsifiers (a) and (b) is 16-25% by weight, based on the emulsion.

4. The emulsion of claim 1, wherein the weight ratio of the components (a:b) is in the range (2.5-3.5):1.

5. The emulsion of claim 1, wherein said hydrotrope (e) is selected from the group consisting of glycerol, butylene glycol and propylene glycol.

6. The emulsion of claim 1, wherein said metal soap (f) comprises magnesium stearate and/or aluminum stearate.

7. The emulsion of claim 1, further comprising at least one irritation-relieving active substance.

8. The emulsion of claim 1, wherein said emulsion has a viscosity of 500-5000 mPa·s at 23° C.

9. The emulsion of claim 1 which, when coated on papers and/or nonwovens, decreases whiteness of the paper and/or nonwoven by not more than 4%.

10. The emulsion of claim 8, wherein said emulsion has a viscosity of 500-3000 mPa·s at 23° C.

11. The emulsion of claim 8, wherein said emulsion has a viscosity of 1000-2000 mPa·s at 23° C.

* * * * *